United States Patent
Tarro

(10) Patent No.: US 6,664,378 B1
(45) Date of Patent: *Dec. 16, 2003

(54) UROGENITAL CARCINOMA ANTI-TLP PEPTIDE ANTIBODIES, RELATED KITS AND METHODS

(75) Inventor: Giulio Tarro, Rome (IT)

(73) Assignee: Unihart Corporation, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 09/661,503

(22) Filed: Sep. 14, 2000

Related U.S. Application Data

(62) Division of application No. 09/051,357, filed as application No. PCT/IT97/00158 on Jul. 2, 1997, now Pat. No. 6,222,010.

(30) Foreign Application Priority Data

Jul. 10, 1996 (IT) ......................... RM96A0496

(51) Int. Cl.[7] ........................ C07K 16/30; C07K 16/18; G01N 33/53; G01N 33/574

(52) U.S. Cl. ................ 530/387.9; 530/387.1; 530/387.7; 530/388.1; 530/388.15; 530/388.8; 530/388.85; 530/389.1; 530/389.7; 435/7.1; 435/7.2; 435/7.21; 435/7.23; 436/501; 436/503; 436/504; 436/63; 436/64

(58) Field of Search ............... 530/387.1, 387.7, 530/387.9, 388.1, 388.15, 388.8, 388.85, 389.1, 389.7; 435/7.1, 7.2, 7.23, 7.21; 436/501, 503, 504, 63, 64

(56) References Cited

FOREIGN PATENT DOCUMENTS

| EP | 0283443 | | 9/1988 |
|----|---------|---|--------|
| EP | 0 283 443 | * | 9/1988 |
| WO | 9401458 | | 1/1994 |
| WO | 9801462 | | 1/1998 |

OTHER PUBLICATIONS

Garaci et al., 1996, "A New Tumour Associated Antigen of Non–Small Cell Lung Cancer: Tumour Liberated Proteins (TLP)—A Possible New Tumor Marker"; *Anticancer Research* 16: 2253–2256.

Tarro et al., "Antigenic Regions of Tumor Liberated Protien (TLP) Complexes and Antibodies Against the Same", *Biomedicine and Pharmacotherapy*, 47:290.

Tarro et al., 1983, "Human Tumor Antigens Inducing in vivo Delayed Hypersensitivity and in vitro Mitogenic Activity"; *Oncology* 40: 248–254.

* cited by examiner

*Primary Examiner*—Anthony C. Caputa
*Assistant Examiner*—Anne L. Holleran
(74) *Attorney, Agent, or Firm*—Baker Botts L.L.P.

(57) ABSTRACT

An antibody that binds to a specific urogenital carcinoma tumor liberated protein (TLP) epitope, wherein the TLP comprises GlyProProGluValGlnAsnAlaAsn, is described. Also described are kits comprising the antibody, and methods of identifying TLP, and methods for diagnosing urogenital carcinoma.

4 Claims, No Drawings

UROGENITAL CARCINOMA ANTI-TLP PEPTIDE ANTIBODIES, RELATED KITS AND METHODS

This is a divisional of U.S. patent application Ser. No. 09/051,357, filed Apr. 15, 1999, now U.S. Pat. No. 6,222,010 which is a U.S. national stage application based on International Application No. PCT/IT97/00158, filed Jul. 2, 1997, which claims priority of Italian Patent Application No. RM96A000496, filed Jul. 10, 1996.

The present invention concerns peptides of the TLP complex (tumour released proteins) isolated from urogential carcinoma.

In particular the invention refers to peptides of TLP protein complexes from human urogential carcinoma having antigenic activity and to antibodies able to react with them, to be used in diagnostics and clinics.

TLP complexes are protein complexes which are present in human tumor cells. Among TLP proteins a 214 KDa protein is described (Tarro G., Oncology 40, 248–253, 1983). TLP are isolated from tumor tissues as described in the European Patent EP 283443. Italian Patent Application No. RM92A000506 identifies a TLP protein from lung carcinoma. The author of the instant invention has surprisingly found that TLP from urogential carcinoma comprise new peptides having sequences which differ from known TLP peptides.

Therefore there is the need to identify TLP peptides, acting as epitopes, from urogenital carcinoma, to produce specific reagents, as antibodies.

The author of the instant invention has identified a peptide having a sequence comprised in the sequence of the 214 kDa TLP protein from either cervix, uterus, or testis adenocarcinoma, and from kidney neoplasia.

Therefore it is an object of the instant invention a peptide comprising a specific urogenital carcinoma TLP epitope, wherein said TLP is characterised by comprising the aminoacid sequence of SEQ ID No. 1:

GlyProProGluValGlnAsnAlaAsn.

According to a preferred embodiment the peptide comprises the aminoacid sequence of SEQ ID No. 1.

Further objects of the invention are specific reagents able to recognise the TLP from urogenital carcinoma, preferably said reagents comprise TLP antibodies. More preferably said antibodies recognise the peptide fragment having the sequence of SEQ ID No. 1.

Further objects of the invention are diagnostic kits to identify TLP from a sample comprising as specific reagents the antibodies of the invention.

Another object of the invention is a pharmaceutical composition comprising as active agent the peptide of the invention.

The invention will now be described according to exemplificating but not limiting examples.

EXAMPLE 1

Preparation of Tumoral Extract

A tumor biopsy of 12,55 g, from a 45 old woman having a cervix carcinoma, was thawed at room temperature and necrotic tissues were surgically removed. When the material resulted to be homogeneous, many washings were performed with Tris 1×(10 mM Tris-HCl pH 7.2) and the tissue subjected to three freeze-thawing cycles.

Used Tris washing solution was collected and centrifuged at 33,000 rpm for 1 hr. The supernatant was collected and frozen.

The tissue was sonicated three times for three min. and subsequently ultracentrifuged at 33,000 rpm for 120 min. The supernatant (5,7 ml) was collected, filtered on Agrodisc filters (0.45 μm), and the tissue was suspended to a ratio of 1 g/ml Tris, and ultracentrifuged at 33,000 rpm for 60 min. The supernatant (0.5 ml) was filtered and added to the previous one.

The same process was performed on either testicular carcinoma (total yield 1.9 ml) or kidney neoplasia samples.

EXAMPLE 2

Identification of Peptides Comprised in the TLP Protein from Urogential Carcinoma The TLP complex is isolated from urogential carcinoma extracts as described in the EP 283443 patent. Samples utilised are:

1) cervix adenocarcinoma;

2) testicular carcinoma;

3) kidney neoplasia.

The protein content resulted to be as follows:

TABLE 1

| Sample | Total mg | mg/ml TLP |
|---|---|---|
| cervix adenocarcinoma | 59,5 | 9,6 |
| testicular carcinoma | 7,4 | 3,9 |
| kidney neoplasia | 7,4* | 1,5 |

*Total kidney protein concentration did not allow an efficient TLP purification yield.

The TLP identification was performed through molecular weight determination (214 kDa) by means of denaturing electrophoretic analysis (SDS).

The removal of the main part of contaminants was performed by taking off gel sections corresponding to an apparent molecular weight of 214 kDa and by further electroeluting with a microelectroelution apparatus (AMICON).

Subsequently the TLP purity was confirmed by denaturing electrophoresis analysis. TLP was then transferred onto a PVDF (polyvinylidifluoride) membrane with an high protein capturing activity, and a sequential aminoacid analysis according to the Edman method was performed, with a protein automated sequencing apparatus by Applied Biosystems.

The aminoacid sequence which was found in all of samples was the following: GlyProProGluValGlnAsnAlaAsn (SEQ ID No.1).

What is claimed is:

1. An antibody that binds to a peptide, wherein the amino acid sequence of the peptide consists of SEQ ID NO:1.

2. A diagnostic kit for identifying tumor liberated proteins of a urogenital tumor sample comprising the antibody of claim 1.

3. A method for identifying tumor liberated proteins in a urogenital tumor sample comprising the steps of:
   (a) combining tumor liberated proteins of a urogenital tumor sample with an antibody according to claim 1 under conditions which would allow immunoprecipitation of antibody-reactive tumor liberated proteins to occur; and
   (b) detecting the presence of immunoprecipitated tumor liberated proteins by detecting the presence of the antibody.

4. A method for diagnosing urogenital carcinoma in a subject, comprising the steps of:
   (a) obtaining a sample from the subject;
   (b) combining the sample with an antibody according to claim 1 under conditions which would allow immunoprecipitation of antibody-reactive tumor liberated proteins to occur; and
   (c) determining whether or not immunoprecipitated tumor liberated proteins are present by detecting the presence of the antibody;
wherein the presence of tumor liberated proteins has a positive correlation with the presence of urogenital carcinoma.

* * * * *

UNITED STATES PATENT AND TRADEMARK OFFICE
CERTIFICATE OF CORRECTION

PATENT NO. : 6,664,378 B1 Page 1 of 1
DATED : December 16, 2003
INVENTOR(S) : Tarro Giulio It is certified that error appears in the above-identified patent and that said Letters Patent is hereby corrected as shown below:

Title page,
Item [56], References Cited, OTHER PUBLICATION, "Tarro et al." reference (first occurrence), "Protien" should read -- Protein --

Column 1,
Lines 13, 16 and 27, "urogential" should read -- urogenital --
Line 21, "KDa" should read -- kDa --
Lines 40, 41 and 45, "aminoacid" should read -- amino acid --
Line 47, "carcinoma, preferably" should read -- carcinoma. Preferably --
Lines 58-59, "exemplificating" should read -- exemplifying --
Line 64, "Tumoral" should read -- Tumor --
Line 66, "12,55 g," should read -- 12.55 g, --; and
    "40 old" should read -- 40-year-old --

Column 2,
Line 12, "5,7 ml" should read -- 5.7 ml --
Line 26, "Urogential" should read -- Urogenital --
Line 28, "urogential" should read -- urogenital --
Table 1, ","(comma) all (six) occurrences, should read --. -- (decimal point)
Line 59, "polyvinylidifluoride" should read -- polyvinylidenefluride --
Lines 60 and 65, "aminoacid" should read -- amino acid --

Signed and Sealed this

Twenty-seventh Day of July, 2004

JON W. DUDAS
*Acting Director of the United States Patent and Trademark Office*

```
                           SEQUENCE LISTING

<160> NUMBER OF SEQ ID NOS: 1

<210> SEQ ID NO 1
<211> LENGTH: 9
<212> TYPE: PRT
<213> ORGANISM: Homo Sapiens

<400> SEQUENCE: 1

Gly Pro Pro Glu Val Gln Asn Ala Asn
 1               5
```